(12) United States Patent
Spurrell

(10) Patent No.: US 6,514,721 B2
(45) Date of Patent: Feb. 4, 2003

(54) AIR SAMPLER FOR PATHOGENS AND PSYCHROMETRICS

(75) Inventor: Leon Bryan Spurrell, Etobicoke (CA)

(73) Assignee: Biochem Technologies, Inc., Etobicoke (CA)

( * ) Notice: Subject to any disclaimer, the term of this patent is extended or adjusted under 35 U.S.C. 154(b) by 0 days.

(21) Appl. No.: 09/898,715

(22) Filed: Jul. 3, 2001

(65) Prior Publication Data

US 2003/0005761 A1 Jan. 9, 2003

(51) Int. Cl.$^7$ .............................. C12Q 1/24; C12Q 1/22
(52) U.S. Cl. .................. 435/30; 435/31; 435/307.1; 435/287.5; 435/288.3; 73/29.02; 73/335.06
(58) Field of Search ................. 435/30, 31, 307.1, 435/308.1, 287.5, 288.3; 73/29.02, 335.06

(56) References Cited

U.S. PATENT DOCUMENTS

| | | | |
|---|---|---|---|
| 3,795,135 A | 3/1974 | Andersen ........................ 73/28 |
| 4,663,293 A | 5/1987 | Hempel et al. ............... 435/294 |
| 5,148,710 A | * 9/1992 | Gudehus et al. ......... 73/335.06 |
| 5,333,511 A | 8/1994 | Boyum et al. ............ 73/864.34 |
| 5,500,369 A | 3/1996 | Kiplinger ................. 435/309.1 |
| 5,766,958 A | 6/1998 | Sullivan et al. ............. 436/174 |
| 6,014,890 A | * 1/2000 | Breen ......................... 73/29.02 |
| 6,054,324 A | 4/2000 | Sullivan et al. ............. 436/174 |

OTHER PUBLICATIONS

Spiral Biotech, "On line catalog cut sheet for Burkard Microbial Air Samplers," Burkard Portable Air Sampler, (May 2, 2001).

* cited by examiner

Primary Examiner—Louise N. Leary
(74) Attorney, Agent, or Firm—Kirk A. Wilson

(57) ABSTRACT

An air sampler device and method for collecting airborne pathogens and psychrometric data for room or remote air samples wherein the sample volume is electronically controlled. Particulates in the air are caused to impact the surface of the growth/inhibitor media contained in the pathogen dish thereby depositing pathogenic microorganisms in the media. The growth/inhibitor media may be a solid, liquid, gel, or mixture thereof. After the pathogen dish is incubated, colony forming units are counted for determination of air quality parameters. A chip-based sensor measures psychrometric properties of the air sample.

16 Claims, 7 Drawing Sheets

AIR SAMPLER FOR PATHOGENS AND PSYCHROMETRICS

FIELD OF THE INVENTION

This invention relates generally to air samplers and, more particularly, to an air sampler assembly for collecting airborne pathogens and psychrometric data from a room or remote locations wherein the sample volume is electronically controlled.

BACKGROUND OF THE INVENTION

The air inside buildings often is contaminated with particles and chemicals that adversely affect the health of the occupants. These pollutants have been brought indoors from the outside or arise from sources indoors. Airborne pathogens, sometimes referred to as biological contaminants or aerosols include;
1. Infectious agents such as bacteria, viruses, and fungi which may cause tuberculosis; legionellosis; Pontiac fever; measles; influenza; colds; aspergillosis; coccidioidomycosis; histoplasmosis; and
2. Allergenic agents such as bacteria, fungi, insects, algae, pollen, animals, and products of microbiological metabolism that may cause sensitivity to B. subtills; allergic asthma; rhinitis; hypersensitivity to molds; sensitivity to house dust mites, cockroaches, houseflies, moths, carpet beetles, aphids, crickets, mosquitoes, and weevils; hypersensitivity reaction to endotoxins from gram-negative bacteria, cotton dust (some mycotoxins are potent carcinogens); hayfever from ragweed pollen; sensitivities to grass and tree pollens; and allergic rhinitis and asthma from bird and mammal dusts.

The pathogens often manifest themselves as human health symptoms such as mucus membrane irritation, headache, and fatigue. These symptoms are associated with what is termed the "sick building syndrome." Biological aerosols have been the predominant cause of complaints in 1–5% of problem office buildings investigated by the U.S. National Institute for Occupational Safety and Health (NIOSH). Airborne biological contamination may be a larger problem in homes where there is a greater variety of source materials and very different types of activities that contribute to the presence of microorganisms, and plant and animal matter.

Assessment of biological aerosols in studies of indoor air quality requires knowledge of many specialties because complaints may be due to aerosols of bacteria, viruses, fungi, algae, house dust mite particles, or pollen grains. One may also need advice from epidemiologists, statisticians, and from medical professionals to diagnose infections and allergies. An understanding of ventilation systems and the movement of air through buildings is also essential, as is a knowledge of how small particles travel through the air and how they can be collected, identified, and quantified. Psychrometric properties of air such as relative humidity, absolute humidity, and dry bulb temperature help determine ambient conditions suitable for growth of pathogens. Building pressurization information helps identify the pathogen source and subsequent remediation options.

A vast array of sampling instruments has been developed for airborne microorganisms. A summary of a number of devices of this type can be found in Air-Sampling Instruments for Evaluation of Atmospheric Contaminants, 8th Edition (1995), American Conference on Governmental Industrial Hygienics. Two of these instruments, the Andersen cascade impactor and the all-glass impinger, have proven useful and reliable enough to be considered standard sampling instruments. The Andersen cascade impactor has remained popular, because it is convenient to use pre-poured plates, the distribution of particle sizes can be determined, and the sampling rate is fairly high (28 L/min). Liquid impingers are used when the organisms require rapid rehydration, to collect soluble materials, e.g., Tyco- or bacterial endo-toxins and some antigens, or when the total number of cells must be determined rather than the number of contaminate particles. Readily-identifiable pollen grains, algal cells, fungal spores, and fragments of nonviable organisms can be collected with a rotorod sampler or on air filters for identification with a light or electron microscope.

After suspended particles have been collected on or in a suitable medium, the viable microorganisms, those that will multiply when provided the appropriate conditions, contained in or on these particles can then be counted and identified. The techniques used to extract viable cells and particles carrying them from the air are also used by environmental scientists looking for nonviable particles. The most efficient methods of removing suspended particles from the air, e.g., filtration through fine pore matrices, might be adequate for resistant forms of microorganisms, such as spores, but can damage less environmentally resistant, vegetative cells. The absence of these sensitive cells from a sample could cause one to mistakenly conclude that they were not present in the environment sampled. The total number of cells present can be estimated by microscopic examination of collected dust, sometimes with the help of stains or fluorescent tags. NIOSH has suggested the following indoor concentrations of bacteria and fungi as indicative of situations deserving of further attention: air concentration>103 colony-forming units per cubic meter (cfu/m3), dust samples>105 cfu/g, water samples >105 cfu/ml.

The proposed NIOSH sampling protocol uses the last stage of the Andersen impactor to collect samples onto standard petri dishes of medium. Different media are used for collecting fungi and bacteria. The total number of viable particles is reported, and when useful, the isolates are identified. This procedure will identify cases of heavy contamination, but further tests might be needed in some situations. A more comprehensive approach would include using a spore trap with visual identification of spores and pollen in the collected dust, a viable sampler with at least three types of culturing media, and a filter or a liquid impinger sample for bioassays, biochemical tests, and immunological analyses.

The accurate measurement of the gas flow rate is very important in air filter sampling because the contaminant concentration is determined by the ratio of the sampled contaminant quantity to the sampled air volume. One widely used conventional flowmeter in air sampling is the rotameter. Rotameters are sensitive to pressure changes in upstream and downstream airflows. Most flowmeters are calibrated at atmospheric pressure, and many require pressure corrections when used at other pressures. When the flowmeter is used in air sampling, it should be downstream of the filter to exclude the possibility of sample losses in the flowmeter. Therefore, the sampled air is at a pressure below atmospheric due to the pressure drop across the filter. Furthermore, if the filter resistance increases due to the accumulation of dust, the pressure correction is not a constant factor. During the sampling period, the filter tends to be plugged and the flow rate may decrease as filter resistance increases. These factors make it difficult to measure the flow rate accurately.

Critical orifices have been widely used in flow rate control for air sampling because they are simpler, reliable and inexpensive. When the pressure drop across the critical orifice is more than 47% of the upstream pressure, the speed of sound is achieved in the throat and the velocity will not change with a further reduction in downstream pressure. Under these conditions, the flow rate is kept constant if upstream conditions are constant. However, commercially available orifices were found to lack the required precision and accuracy because they differed from the nominal flow-rate by up to 15%. Another disadvantage of most critical orifice designs is that a pressure drop in excess of 47 kPa is required to ensure a stable flow. To achieve this pressure drop, a special high power vacuum pump must be used. Some commercial flow limiting orifices even require a vacuum as high as 72 kPa.

BRIEF SUMMARY OF THE INVENTION

A portable device and method for collecting an electronically controlled sample of air that impacts a pathogen dish mounted substantially transverse to the overall airflow pattern to capture airborne pathogens and further having a psychrometric sensor that measures psychrometric properties of the air sample. Particulates in the air are caused to impact the surface of the growth/inhibitor media contained in the pathogen dish thereby depositing pathogenic microorganisms in the media. The growth/inhibitor media may be a solid, liquid, gel, or mixture thereof. A chip-based sensor measures psychrometric properties of the air sample.

Room air is sampled through a calibrated perforated impactor plate. Remote air samples are collected through a calibrated remote sensor assembly.

An advantage of the invention is the means for controlling the sample volume wherein the fan is activated and controlled for a predetermined time period programmed for the specific type of sample being collected. Each remote collection assembly and each room air collection assembly has a specific control algorithm designed for the entire collection device. All components are low airside pressure drop items to enable using of a small, low power fan.

Another advantage of the invention is the ability to collect airborne pathogen data and psychrometric data simultaneously thereby providing more complete information on the quality of the air being sampled.

Another advantage of the invention is that the sampler is simple, inexpensive, and portable. Rechargeable battery power allows the sampler to be used at any location and multiple samples can be drawn with a single battery charge. Each sample may contain a different growth/inhibitor media for collection of spores, pollen, dust, pathogens, and bioassays.

DETAILED DESCRIPTION

Figure 1:
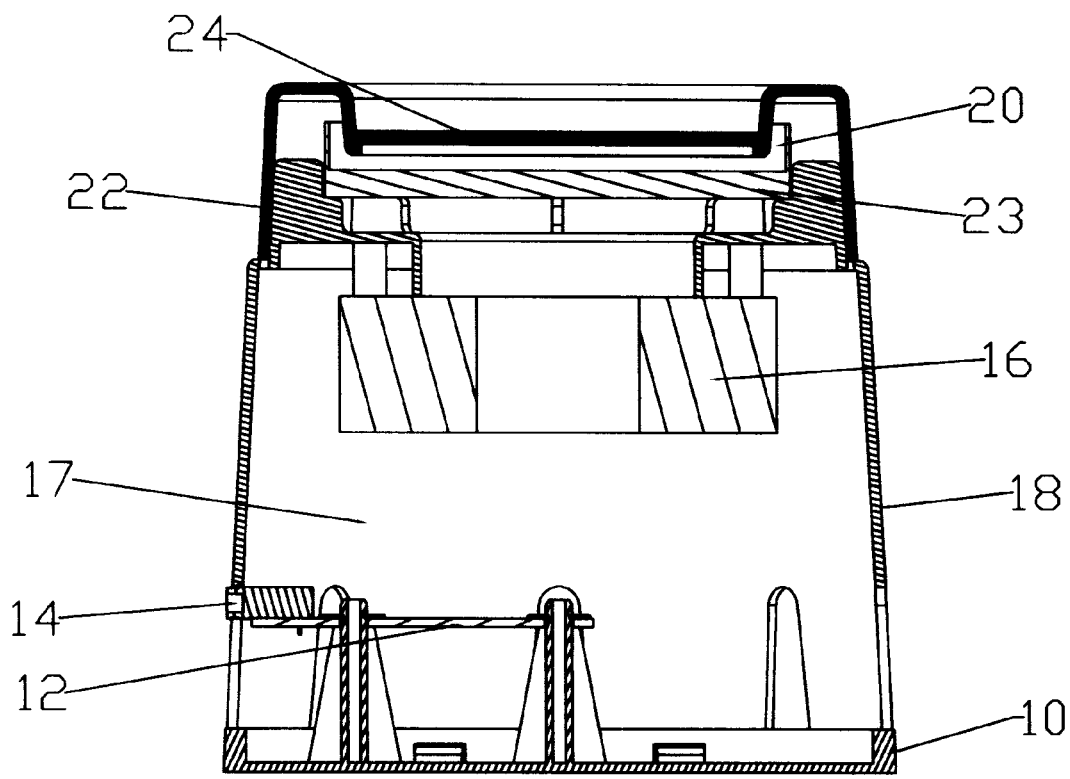
FIG. 1 is a side view of the room air sampler.

An integrated air sampler and psychrometric sensor is used to detect airborne pathogens and associated psychrometric properties of the air sample in order to identify pathogenic indoor air pollutants and the sources of those pollutants. The sample volume is controlled by knowing the static pressure imposed on the fan by the sampler components and determining the flow rate from the fan performance curve. The fan is then electronically controlled and timed to stop when a preselected volume of air has been sampled.

EXAMPLE

The sampler fan delivers 10 liters per minute (LPM) of standard temperature and pressure (STP) air at 0.5 inches water gage (WG) external static pressure according to the certified fan performance curve at 1800 revolutions per minute (RPM). The external static pressure imposed on the fan by the sampler components is 0.5 inches WG. The preselected sample volume is 20 liters, therefore, sample run time is 2 minutes for the 10 LPM flow rate. The electronic flow controller measures the current to the sampler fan motor to maintain 1800 RPM for 2 minutes before shutting down the fan motor. The entire 20-liter air sample impacts the pathogen dish and deposits particulate on the growth/inhibitor media for determination of colony forming unit (CFU) counts. Downstream of the pathogen dish, the psychrometric sensor measures relative humidity, absolute humidity, and dry bulb temperature, displays the data on an LED readout device mounted on the air sampler casing, and stores the data for later downloading. After the first sample is complete, the pathogen dish is removed and replaced with a clean dish, the electronic flow controller is reset, and another sample is taken.

The electrical power source for the sampler is either 120 volts A/C, DC power from a converter or other DC power source, or a rechargeable DC battery.

The psychrometric sensor (e.g. Hygrometrix model HMX 2000) is part of a printed circuit board that senses, stores, and displays relative humidity, absolute humidity, dry bulb temperature, and other psychrometric properties of the sampled air. The printed circuit board is capable of two-way communication with a data acquisition and control system such as a building energy management system. For a specific elevation or atmospheric pressure, two psychrometric properties are measured and the remaining properties are derived from formulas or tables. These air properties determine the ability of the air to support growth of pathogens and other airborne microorganisms.

The growth/inhibitor media comprises a solid, liquid, gel, or mixture thereof and is selected from the group consisting of distilled water, pure water, and agar. Each constituent of a mixture could be in a range from 0% to 99.99% depending on the sampling requirements.

A remote air sample can be taken from a wall cavity, floor cavity, ceiling area, another room, or a specific source point to determine pathogen counts, relative humidity, absolute humidity, and dry bulb temperature thereby enabling determination of building pressure differences, air leakage, building pressurization/depressurization due to stack effect, ventilation system imbalance and the probability of mold growth and structural damage. The psychrometric properties and pathogen counts of air in adjacent building zones and the associated wall cavities or barriers determine the direction of heat and moisture transfer between the zones thereby identifying a potential source of airborne pollutants.

Figure 2:
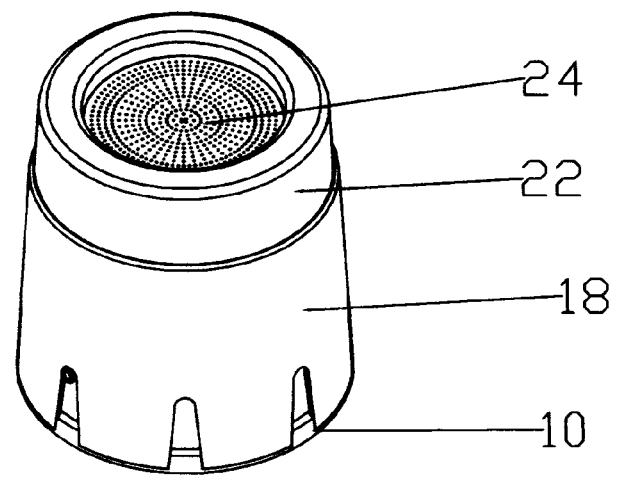
FIG. 2 is an isometric view of the room air sampler.
Figure 3:
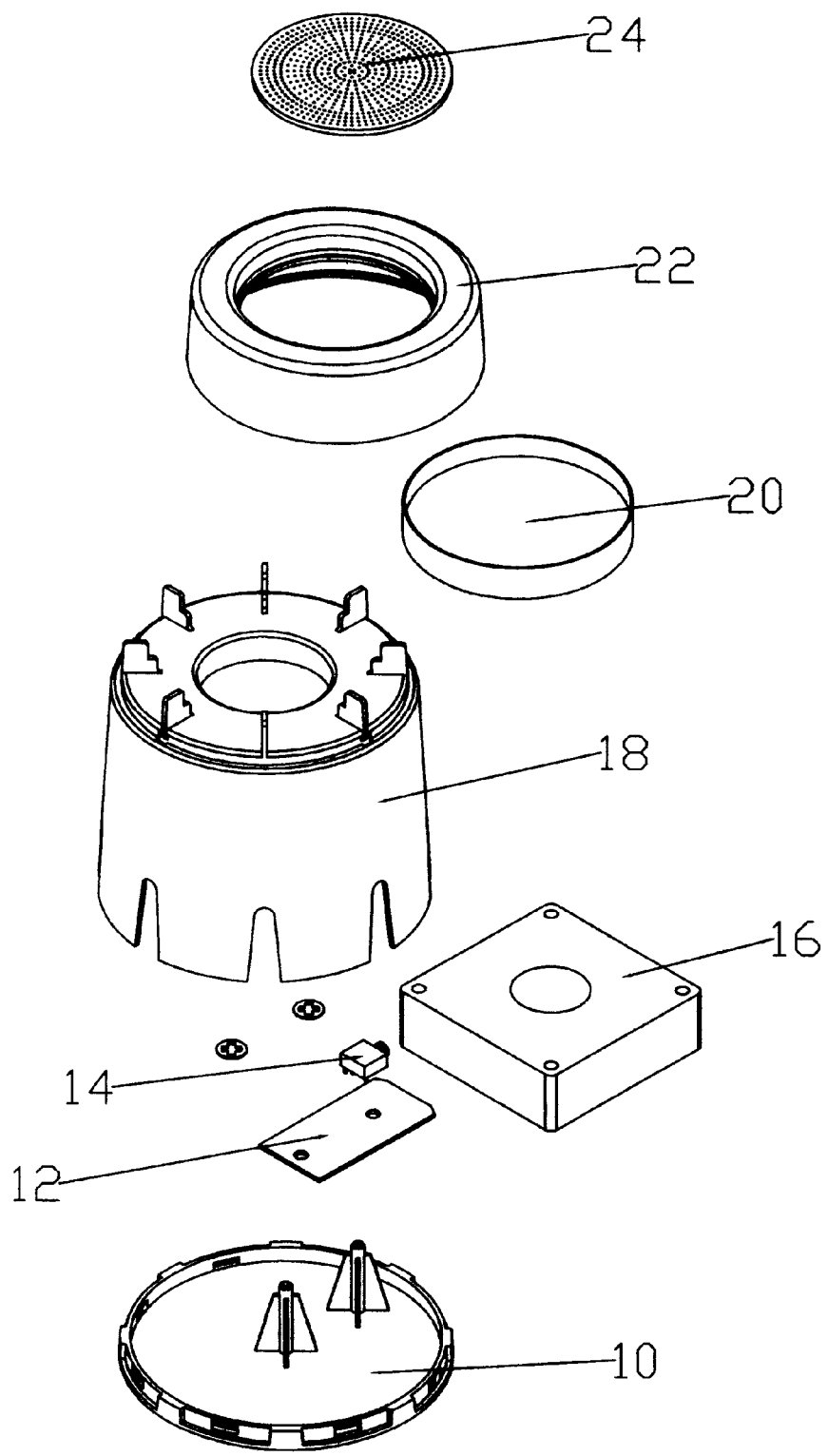
FIG. 3 is an exploded view of the room air sampler showing some of the components.
Figure 4:
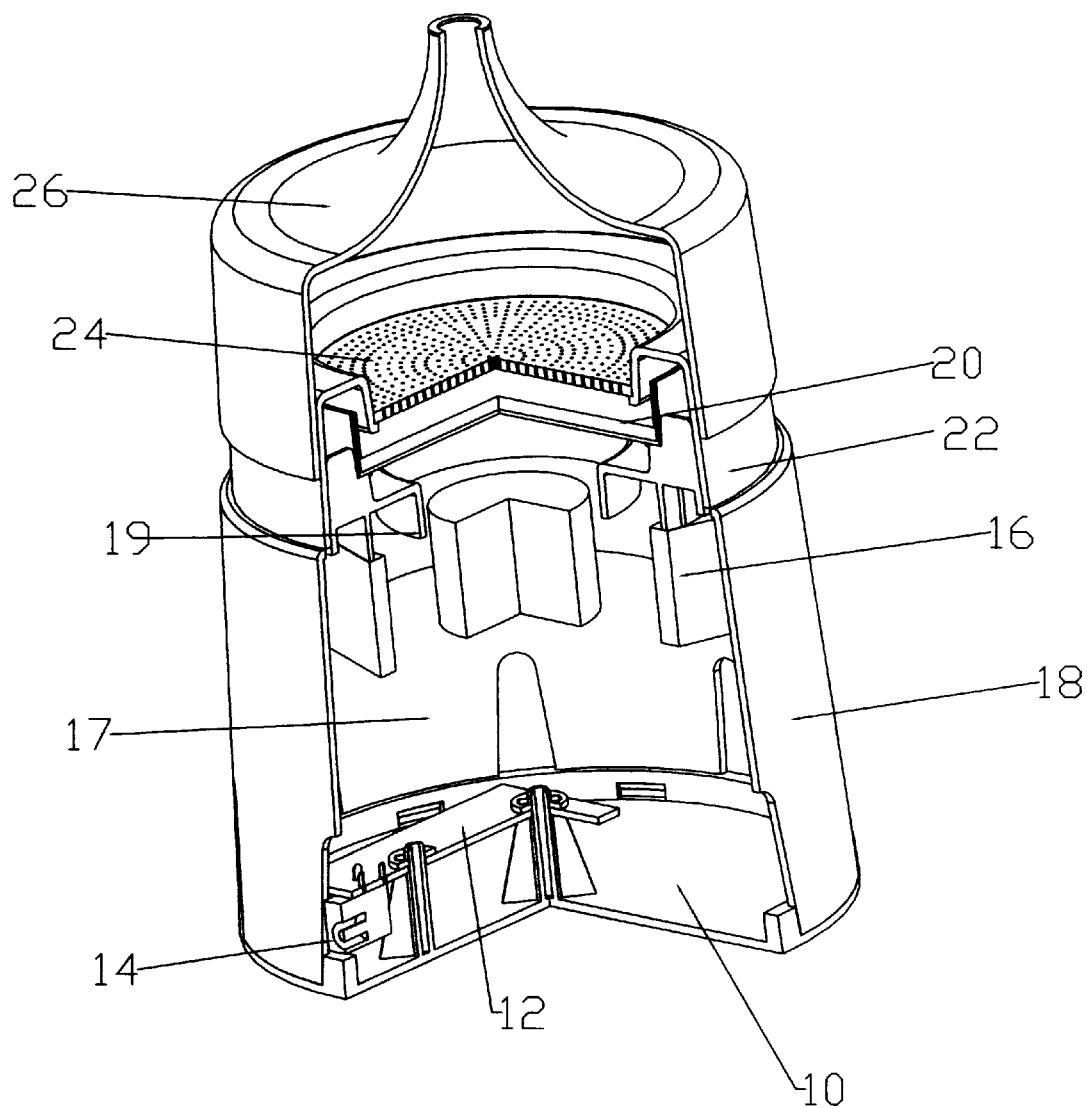
FIG. 4 is an isometric rendering of the remote air sampler.
Figure 5:
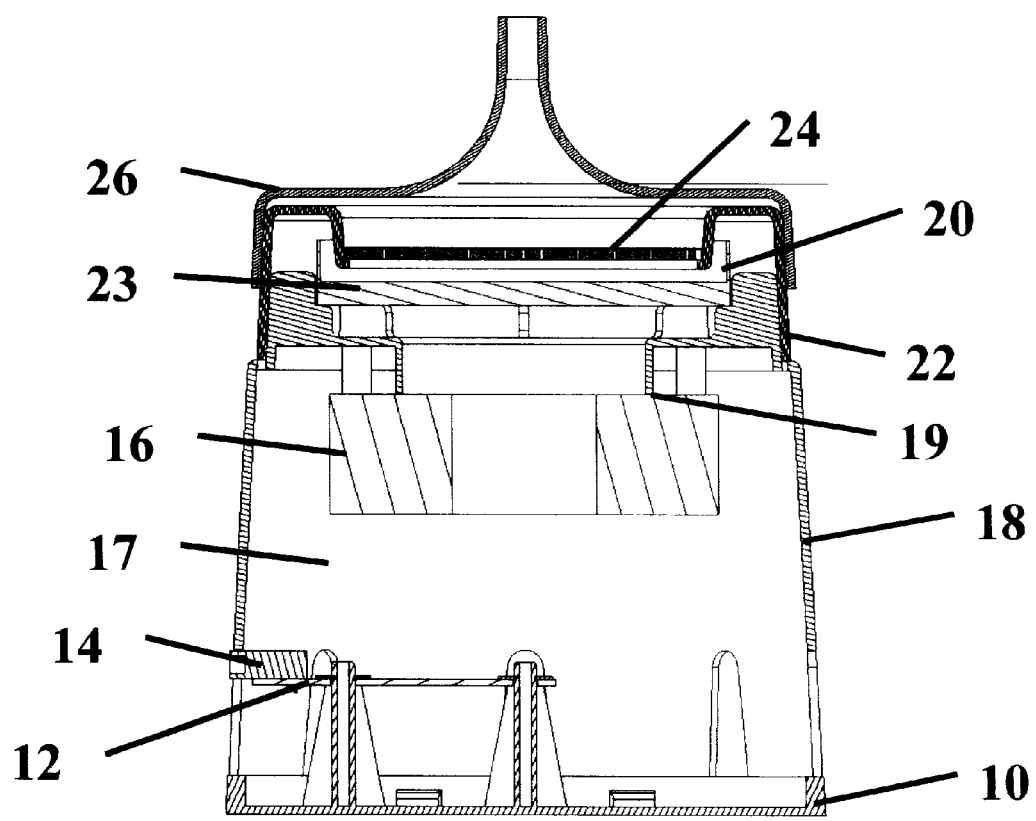
FIG. 5 is side view of the remote air sampler.

FIGS. 1 through 5 show the air sampler base 10, the casing 18, the cap 22 and perforated impact plate 24, all removably attached to form the outer shell of the sampler.

Inside the sample chamber are the printed circuit board 12, the electrical plug 14 with a connector protruding through the casing 18, the fan 16, and the pathogen dish 20. The fan is manually started by a switch (not shown) connected to the printed circuit board 12 or automatically by the program on the printed circuit board 12. The air sample is drawn through the perforated impact plate 24 that is disposed at a preselected distance from the pathogen dish 20. The sample is separated into air jets by the perforated impact plate 24 before impacting the surface of the growth/inhibitor media 23 contained in the pathogen dish 20 thereby depositing particulate matter in the media 23. After impacting the media 23, the air sample disperses radially outward from the media surface and flows over the outer perimeter of the pathogen dish 20 in route to the intake of the fan 16 that is removably attached by an airtight connection 19 directly below the top air inlet of the casing 18. The airtight connection 19 is sealed in a manner to ensure that the sample chamber 17 comprising the printed circuit board 12 and the psychrometric sensor is only exposed to sample air, not ambient air, during the sampling period. The airtight connection 19 also enables sample volume calibration for various flow components on the suction side of the fan, including the remote sampling assemblies, by ensuring that the fan operates at designed flow rate against the full static pressure drop of the suction side components without any air leakage. The air sample then passes through the sample chamber 17 and contacts the printed circuit board 12 for measuring the psychrometric properties of the air sample. These properties are measured, stored, and then displayed on an LED readout device (not shown). The printed circuit board 12 has flash memory for retaining stored data during power interruptions. The printed circuit board 12 is capable of two-way communication with a data acquisition and control system, like a building energy management and control system, such that psychrometric data collected from the sampler can be used to control mechanical systems in buildings. Building zone temperatures and relative humidity as measured by the sampler enable control of airflow quantities, economizer cycles, building pressurization, exhaust/return fans, and other functions in building HVAC systems. The data acquisition and control system can also communicate with the sampler to activate the sampler in a programmed fashion for drawing samples at certain times. The sample then exits the sample chamber 17 through a plurality of side air outlets in the casing 18. After the preselected run time of the fan is completed, which corresponds with a measured sample volume, the printed circuit board resets the counter for the next sample to be drawn. The pathogen dish 20 is changed out for each new sample. The sampler casing 18 is designed to house two different sizes of pathogen dish 20. Automated change-out of the pathogen dish 20 can be performed by mechanical means such that multiple samples can be taken in a preselected time period. The automated change-out can be controlled by the data acquisition and control system.

Figure 6:
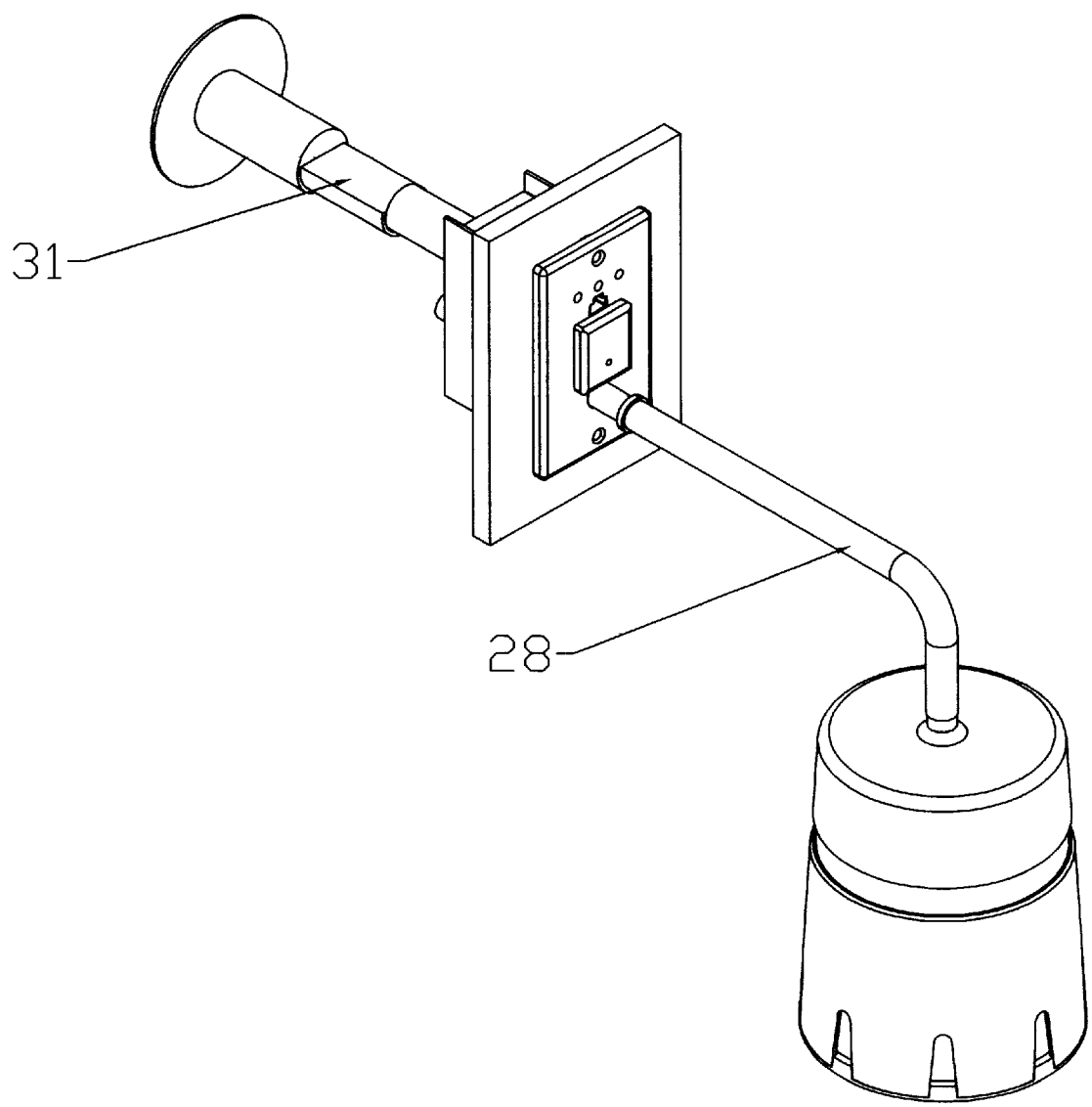
FIG. 6 is an isometric of the remote air sampler connected to the air sampling port of a wall cavity sensor assembly.
Figure 7:
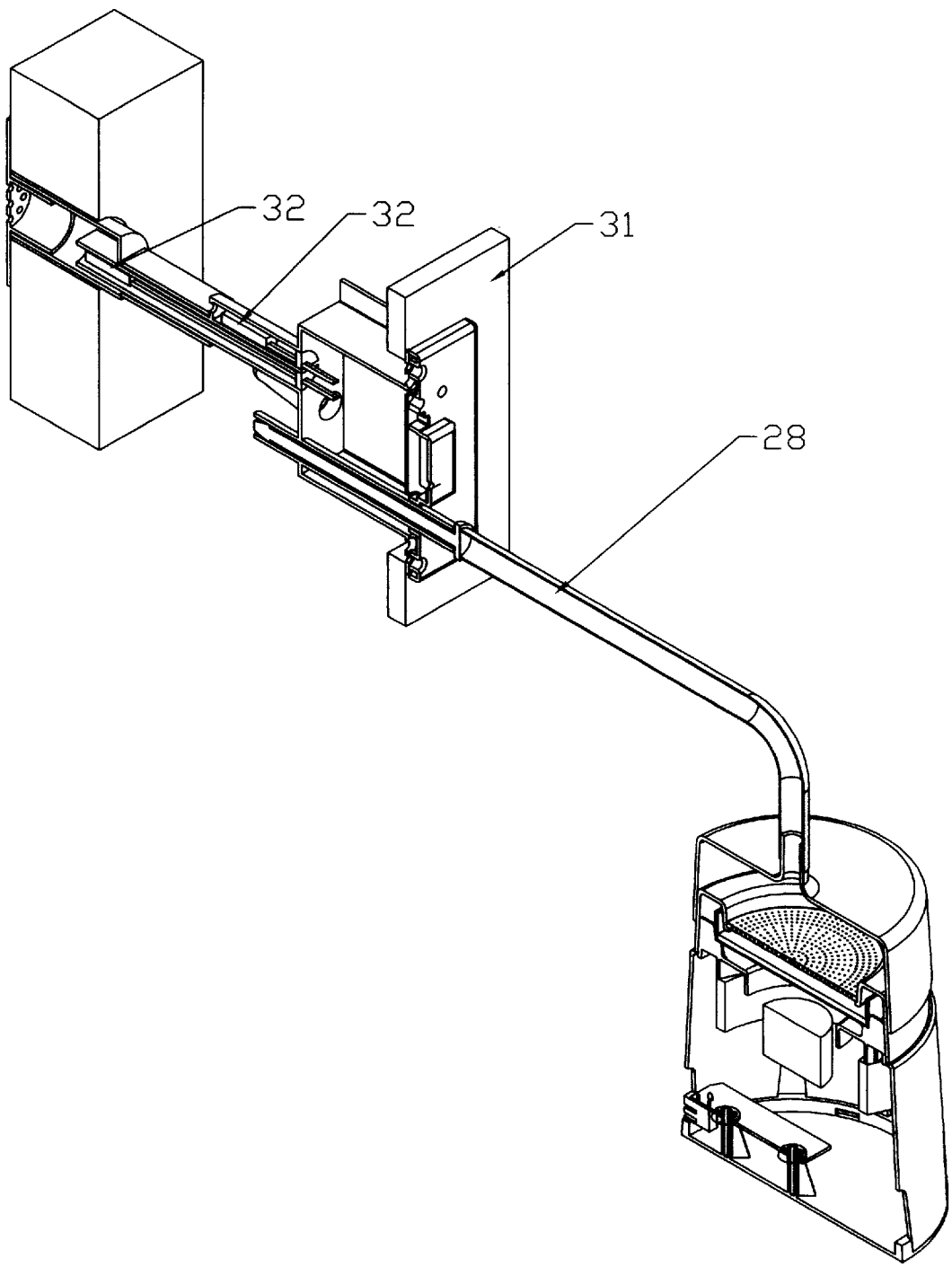
FIG. 7 is an isometric of the remote air sampler connected to a section view of a wall cavity sensor assembly.
Figure 8:
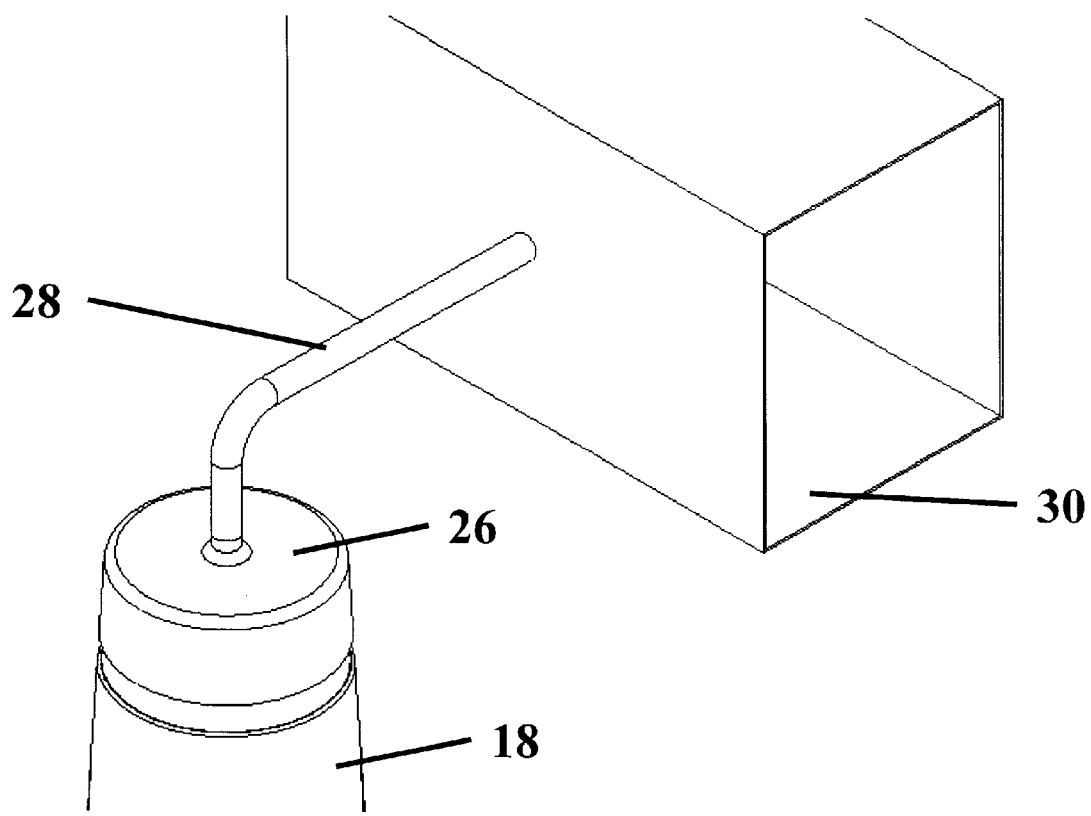
FIG. 8 is an isometric of the remote air sampler connected to a ductwork assembly.

For remote sensing, FIGS. 4 through 8 show a remote sensing assembly comprising the remote sensing head 26 that is removably mounted over the cap 22 to enable interconnected tubing 28 to be run to a remote sensor assembly such as a ductwork section 30 or a wall cavity sensor assembly 31. The wall cavity sensor assembly 31 has an air sampling port enabling fluid communication between the wall cavity and the sampler. Sensor sampling ports in the wall cavity sensor assembly 31 enable separate and specific fluid communication with room air, cavity air, adjacent space air, and other points of interest. Each sensor sampling port houses a psychrometric sensor 32 for measuring air properties. The psychrometric sensors transmit data to a data display, storage, and collection device in the wall cavity sensor assembly that can communicate with a central data analysis system through a wired or wireless communication network. The wall cavity sensor can be adapted and installed in any building structure component including floors, ceilings, partitions, roofs, interior walls, and exterior walls.

The sampler fan run time is programmed for a specific remote sensor assembly that imposes a predetermined external static pressure on the fan 16. Remote locations include such areas as adjacent building spaces, interior and exterior wall cavities, ductwork, and any suspected source spot of airborne contaminants.

Limited embodiments are shown and described for this invention and those skilled in the art will envision other embodiments that are considered part of this invention.

What is claimed is:

1. A portable air sampling apparatus for collecting airborne pathogens and psychrometric data comprising;
    a base,
    a casing removably disposed on said base, said casing having at least one top air inlet and a plurality of side air outlets and a sample chamber disposed between said inlet, outlets, and base,
    at least one pathogen dish removably disposed on said casing above said top air inlet and generally transverse to said top air inlet airflow path,
    a cap removably disposed on said casing, said cap at least partially enclosing said pathogen dish,
    a printed circuit board removably disposed on said base inside said sample chamber,
    a fan removably disposed on said casing and inside said sample chamber,
    a means for controlling said fan,
    a means for measuring psychrometric data inside said sample chamber, and
    a means for communicating with an external data acquisition and control system.

2. The apparatus of claim 1 wherein said pathogen dish comprises a growth/inhibitor media selected from at least one of the group consisting of distilled water, pure water, agar and mixtures thereof.

3. The apparatus of claim 2 wherein said cap further comprises a removable perforated impact plate disposed at a preselected distance from said growth/inhibitor media.

4. The apparatus of claim 3 wherein said cap further comprises a remote collection assembly having a remote sampler head, a remote sensor assembly, and interconnecting tubing.

5. The apparatus of claim 1 wherein said printed circuit board further comprises an electrical plug for supplying alternating or direct current directly to said circuit board or to rechargeable batteries.

6. The apparatus of claim 1 wherein said means for controlling said fan comprises an electronic component on said circuit board that maintains fan speed for a preselected run time.

7. The apparatus of claim 1 wherein said means for measuring psychrometric data comprises an electronic component on said circuit board that senses, stores, and displays relative humidity, absolute humidity, and dry bulb temperature of the air in said sample chamber.

8. The apparatus of claim 1 wherein said means for communicating with an external data acquisition and control system comprises a two-way wired or wireless network.

9. An air sampling method comprising the steps of:
starting the sampler fan, either manually or automatically, with a means for controlling said sampler fan,
impacting said air sample on a cap having a pathogen dish, said pathogen dish further comprising a growth/inhibitor media,
measuring the psychrometric properties of said air sample with a means for measuring psychrometric data located on a printed circuit board inside the sample chamber,
communicating said psychrometric properties with a data acquisition and control system,
removing said pathogen dish from the sampler,
incubating said pathogen dish for a preselected time period in a controlled environment, and
counting the colony forming units in the growth/inhibitor media.

10. The sampling method of claim 9 wherein said pathogen dish comprises a growth/inhibitor media selected from at least one of the group consisting of distilled water, pure water, agar and mixtures thereof.

11. The sampling method of claim 10 wherein said cap further comprises a removable perforated impact plate disposed at a preselected distance from said growth/inhibitor media.

12. The sampling method of claim 11 wherein said cap further comprises a remote collection assembly having a remote sampler head, a remote sensor assembly, and interconnecting tubing.

13. The sampling method of claim 9 wherein said printed circuit board further comprises an electrical plug for supplying alternating or direct current directly to said circuit board or to rechargeable batteries.

14. The sampling method of claim 9 wherein said means for controlling said fan comprises an electronic component on said circuit board programmed to maintain fan speed for a preselected run time.

15. The sampling method of claim 9 wherein said means for measuring psychrometric data comprises an electronic component on said circuit board that senses, stores, and displays relative humidity, absolute humidity, and dry bulb temperature of the air in said sample chamber.

16. The sampling method of claim 9 wherein said communication step is performed by a two-way wired or wireless network.

* * * * *